United States Patent [19]

Schneider et al.

[11] Patent Number: 5,037,623

[45] Date of Patent: Aug. 6, 1991

[54] STERILANT CONCENTRATE INJECTION SYSTEM

[75] Inventors: Edward T. Schneider, Mentor, Ohio; Raymond C. Kralovic, N. Springfield, Pa.

[73] Assignee: Steris Corporation, Mentor, Ohio

[21] Appl. No.: 165,189

[22] Filed: Mar. 7, 1988

Related U.S. Application Data

[63] Continuation-in-part of Ser. No. 826,730, Feb. 6, 1986, Pat. No. 4,731,222.

[51] Int. Cl.$^5$ .................. B01F 13/00; A61L 2/00
[52] U.S. Cl. .................... 422/292; 206/219; 206/532; 422/100; 422/102; 422/294
[58] Field of Search .......... 422/292, 294, 102, 100; 206/219, 532

[56] References Cited

U.S. PATENT DOCUMENTS

| | | |
|---|---|---|
| 675,971 | 6/1901 | Raymond . |
| 854,617 | 5/1907 | Aaron et al. . |
| 2,494,456 | 3/1946 | Still ................................. 128/272 |
| 3,521,745 | 7/1968 | Schwartzman .................. 206/47 |
| 3,713,780 | 1/1973 | Shapiro . |
| 3,893,832 | 8/1975 | Perry et al. ..................... 55/268 |
| 4,171,340 | 10/1979 | Nishimura et al. .............. 422/36 |
| 4,362,241 | 12/1982 | Williams ......................... 206/210 |
| 4,482,047 | 11/1984 | Ackermann et al. ............ 206/219 |
| 4,483,439 | 11/1984 | Steigerwald et al. ........... 206/219 |
| 4,537,303 | 8/1985 | Muhlbauer ..................... 206/219 |
| 4,552,728 | 11/1985 | Taylor ............................. 422/300 |
| 4,794,085 | 12/1988 | Jessop ............................. 436/54 |

FOREIGN PATENT DOCUMENTS

| | | |
|---|---|---|
| 1216770 | 5/1966 | Fed. Rep. of Germany . |
| 2749448 | 5/1979 | Fed. Rep. of Germany . |
| 0088419 | 1/1984 | Fed. Rep. of Germany . |
| 3339930 | 5/1985 | Fed. Rep. of Germany . |
| 547150 | 2/1922 | France . |
| 1100325 | 9/1955 | France . |
| 1304099 | 8/1962 | France . |
| 2138154 | 12/1972 | France . |
| 1180059 | 2/1970 | United Kingdom . |

OTHER PUBLICATIONS

"Raychem: Faster, Better, Quicker" by Alysssa Lappen, Forbes, Nov. 2, 1987, pp. 200-203.

Primary Examiner—Jill Johnston
Attorney, Agent, or Firm—Fay, Sharpe, Beall, Fagan, Minnich & McKee

[57] ABSTRACT

A tubing system (18) connects a source (10) of tap water with a container (20) holding an item to be sterilized. Powdered buffers, detergents, and corrosion inhibitors are deposited in a well (34) along with an ampule (46) containing a sterilant, such as peracetic acid. The ampule includes an exterior wall (80) which defines an interior volume (82) and a linear vent passage (84) extending from the exterior wall to a central region of the interior volume. A gas permeable liquid impermeable membrane (100) is mounted across a vent aperture (86) which is disposed adjacent the geometric center of the interior volume. The volume is filled less than half way full with the liquid sterilant such that in all orientations of the ampule (FIGS. 4A-C), an upper surface (98) of the sterilant remains below the vent aperture. A pump (50) recirculates the water through the container, the tubing system, and the well to dissolve the powdered reagents. A tubular needle (70) of an aspirator system (42) is moved along the vent passage and through the vent aperture such that its free end is immersed in the sterilant. An aspirator (44) draws the sterilant from the ampule into the tubing system, mixing it with the recirculating water.

15 Claims, 7 Drawing Sheets

STERILANT CONCENTRATE INJECTION SYSTEM

This application is a continuation-in-part of U.S. application Ser. No. 826,730, filed Feb. 6, 1986, now U.S. Pat. No. 4,731,222.

BACKGROUND OF THE INVENTION

The present invention relates to ampule systems for maintaining components, particularly reactive components and reagents, separated until immediately prior to use. It finds particular application in conjunction with sterilant systems in which a peracetic sterilant as well as buffers and corrosion inhibitors are diluted or dissolved immediately prior to a sterilizing operation. However, it is to be appreciated that the present invention will find utility in other multi-component systems which are intermixed in preparation for use, such as photographic systems, coating systems, medications, and the like.

Heretofore, most medical facilities have used steam autoclave sterilization systems. Commonly, medical instruments and equipment were transported to a central sterilizing facility where they were sterilized under the supervision of sterilizing room technicians. In a steam autoclave, which typically has a cycle time of one to two hours, the equipment was subject to superheated steam at high pressures. After an appropriate sterilizing duration, the autoclave was depressurized and cooled.

Instruments and equipment which could not withstand the temperature of an autoclave were commonly sterilized with ethylene oxide gas. After the equipment was sealed in a sterilizing chamber, the highly toxic ethylene oxide gas was introduced under pressure and allowed to remain for a couple of hours, as was appropriate to the selected sterilizing cycle. After the sterilizing cycle, the equipment could not be utilized until absorbed ethylene oxide was removed. This generally required about 12 to 16 hours in a vacuum or about 72 hours in ambient atmospheric conditions.

Liquid sterilization systems were also available for equipment which could not withstand the autoclave or the ethylene oxide systems. However, most were manually performed. That is, the equipment was immersed in a vat or tank that had been filled with a sterilizing solution, such as stabilized hydrogen peroxide or glutaraldehyde. However, because long immersion times on the order of 6 to 10 hours, were commonly required for sterilization, the liquid systems were more commonly used for disinfecting. Because the liquid sterilizing or disinfecting agents were toxic to human tissue, the equipment had to be rinsed before it could be used with human patients. Frequently, non-sterile tap water was used as the rinse.

Sterilization connotes the absence of all life forms including bacterial endospores which are the living organisms most resistant to known sterilants. By contrast, disinfection only connotes the absence of pathogenic life forms. As is to be appreciated, establishing the absence of all life forms for sterilization is more readily documented and controlled than the elimination of pathogenic but not all life forms for disinfection.

Because bacterial spores are the life form which is most resistant to sterilants, they are commonly used as a reproducible, stable indicators of the effectiveness of a sterilization product. For medical sterilizers, a sterility assurance level (SAL) of less than or equal to one chance in one million of having an item contaminated by a bacteria spore is generally regarded as the minimum acceptable level for medical devices. In practice, this level of assurance is obtained by a establishing the exposure time required to sterilize a given quantity of bacterial endospores known to be resistant to the sterilant. The destruction rate of the spore is commonly logrythmic. From the logrythmic destruction rate, commonly denoted by a D value, the exposure time required for an insurance level of one in a million ($10^{-6}$) can be readily calculated. Because pathogenic microorganisms, which are mostly vegetative forms of bacteria, do not have the stability to derive a D value or its equivalent, there is no readily available biological indicator to show the effectiveness of a disinfectant.

In accordance with the present invention, a new and improved reactive agent dispensing system is provided which overcomes the above referenced sterilizer problems and analogous problems and other equipment in which reactive agents are released contemporaneously with use.

SUMMARY OF THE INVENTION

In accordance with one aspect of the present invention, a spill resistant, vented ampule is provided. A vent passage defines an vent aperture at one end. A sealed exterior wall defines an interior volume surrounding the vent aperture such that the vent aperture is generally centrally located in the interior volume. The exterior wall is sealed to the vent passage such that the vent aperture provides the only ingress and egress to the interior volume.

In accordance with more limited aspects of the invention, a gas permeable, fluid blocking membrane is mounted across the vent aperture. In this manner, gas is vented from the interior volume but the leakage of fluid is retarded. A volume of a liquid reagent which is less than half of the interior volume is contained within the ampule. The liquid volume is selected such that a top surface of the liquid is below the vent aperture with the ampule disposed in any orientation.

In accordance with another aspect of the present invention, a siphon extraction system is provided for drawing the liquid from the ampule. A small bore tubular member is passed through the vent passage and into the interior volume. The tubular member is connected with an aspirator for withdrawing the liquid from the ampule and intermixing it with a second reagent. In the preferred embodiment, the first reagent is a strong sterilant concentrate such as peracetic acid and the second reagent is a dilutant such as water.

In accordance with another more limited aspect of the present invention, the water and aspirated sterilant concentrate are circulated through a container holding an item to be sterilized and through a tubing system which interconnects the container with a source of sterile rinse water until the item, the interior of the container, and the tubing system are all sterilized. In this manner, the sterile rinse solution cannot carry bacterial contaminants from the tubing into contact with the sterilized item during a rinse portion of the sterilizing cycle.

One advantage of the present invention is that a sterilizing system is provided that assures sterility.

Another advantage of the present invention is that a one dose sterilant cartridge is provided to assure proper reagent formulation and eliminate operator error.

Yet another advantage of the present invention is that it provides a vented, liquid containing ampule which may be disposed in any orientation without leaking liquid.

Still further advantages of the present invention will become apparent upon reading and understanding of the following detailed description.

BRIEF DESCRIPTION OF THE DRAWINGS

The invention may take form in various parts and arrangements of parts or in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
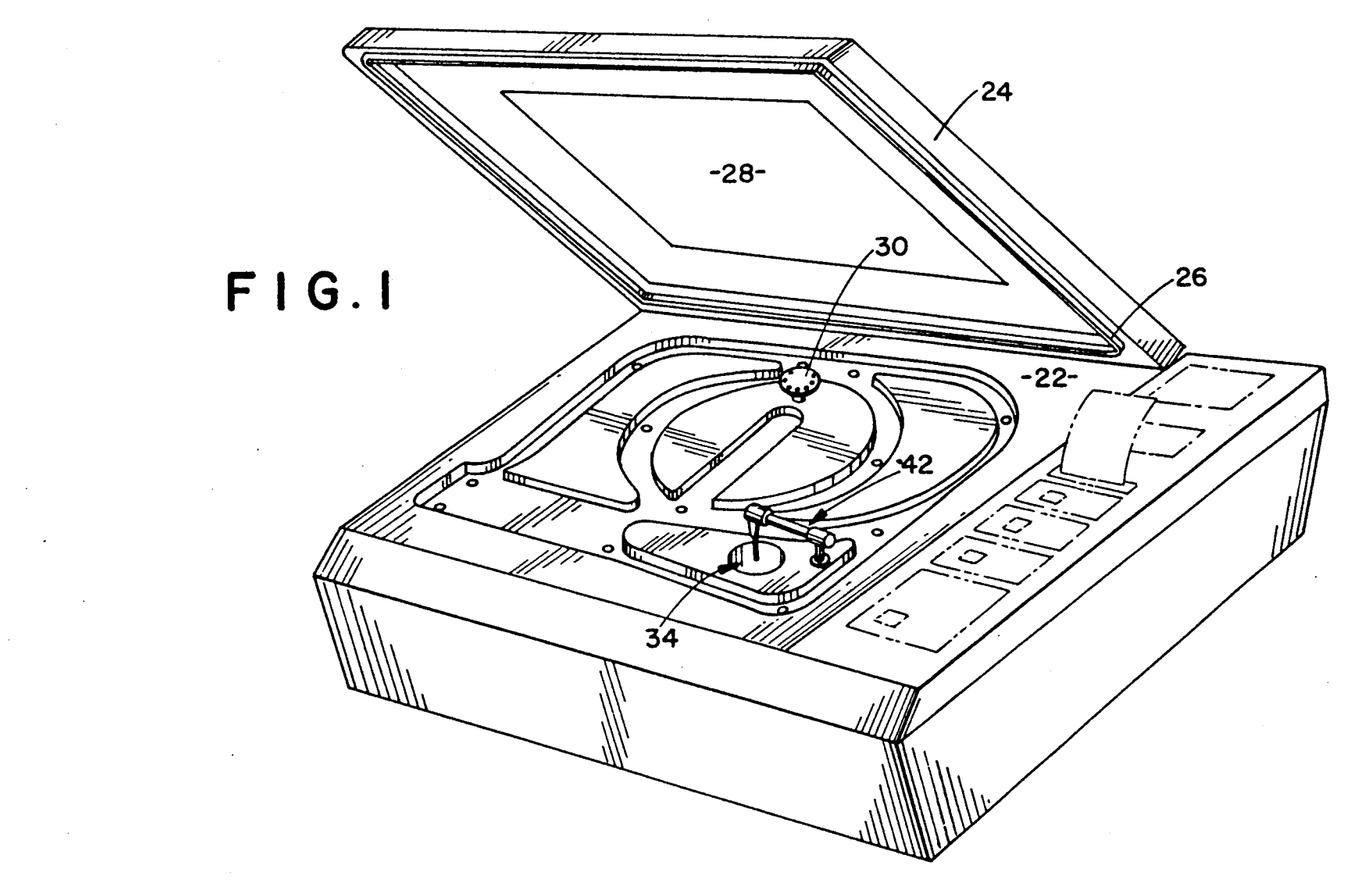
FIG. 1 is a perspective view of a sterilizing apparatus in accordance with the present invention.
Figure 2:
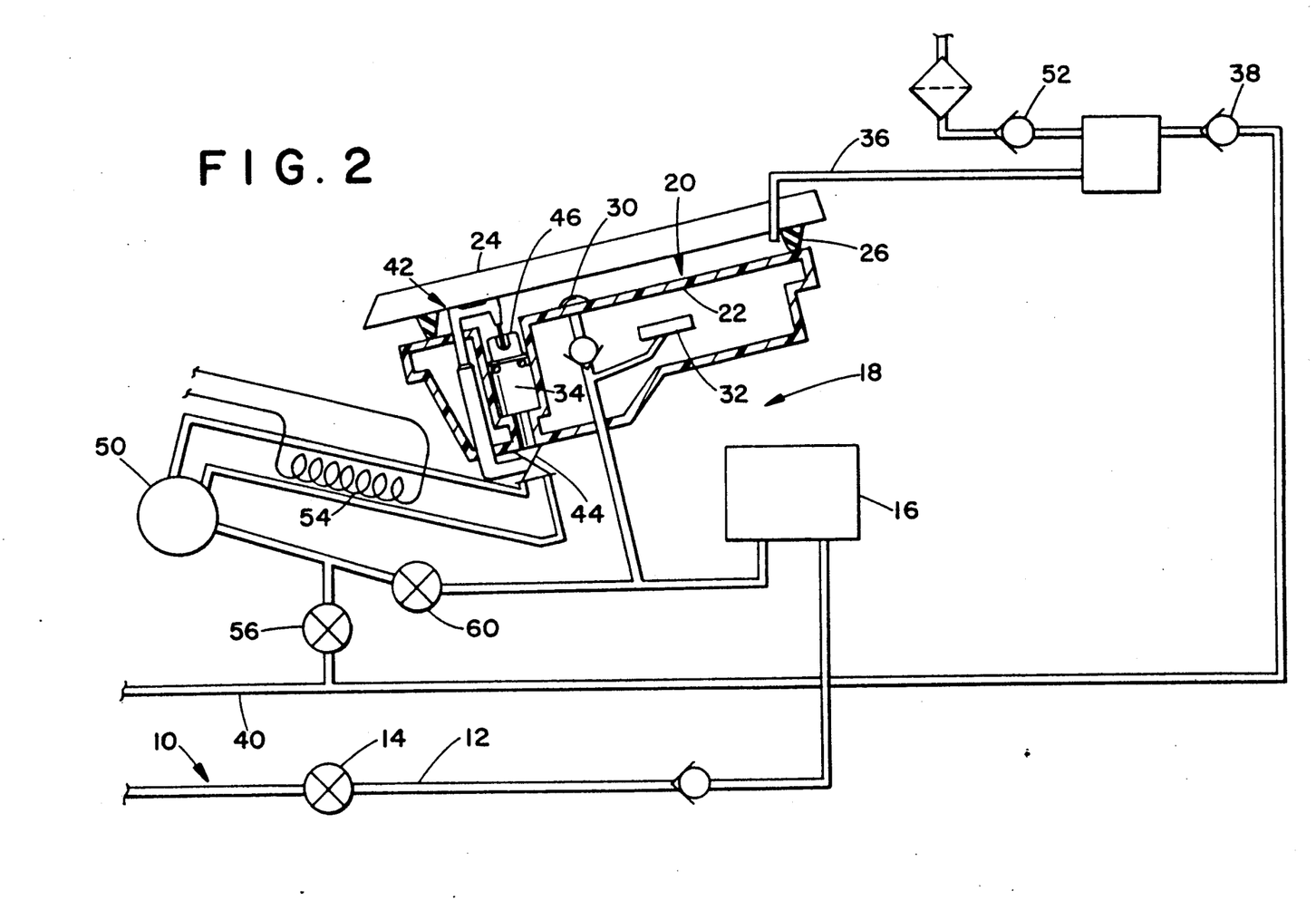
FIG. 2 is a tubing diagram of the sterilizer of FIG. 1.

With reference to FIGS. 1 and 2, a dilutant or water source 10 supplies water or other fluid reagents. In the preferred sterilizer embodiment, the water source includes a length of tubing 12 connected with a water spigot or other building plumbing and a control valve 14 for selectively preventing and permitting the flow of water to a water sterilizing means 16. In the preferred embodiment, the water sterilizing means is a filter which removes particulates which are as large or larger than bacteria.

A tubing system connects the filter with a container or module 20 for receiving an item to be sterilized. In the preferred embodiment, the container is defined by a removable tray 22 configured in accordance with the item to be sterilized, e.g. an endoscope. A lid 24 is sealed to the tray by a resilient gasket 26 to complete the container. Optionally, a transparent window 28 is defined the in the lid.

During a fill cycle, sterile water flows through the tubing system filling itself and the container 20. The water flows through a spray nozzle 30 and a container distribution manifold 32 into the container and a reagent receiving well 34. As more water is introduced, vent lines 36 are filled with excess water and discharged through a check valve 38 into a drain 40.

A reagent introduction system 42 selectively supplies sterilant, buffer, detergent, and corrosion inhibitors to the dilutant. More specifically, an aspirator 44 selectively withdraws sterilant concentrate from an ampule 46. Powdered reagent received in the well 34 is dissolved as water flows in from the container.

After the system is filled, pump 50 selectively draws water from the container 20 through the well 34 and aspirator 44. Recirculating the water dissolves the powdered reagents and aspirates the sterilant from the ampule and circulates the sterilant and reagents through the tubing system 18. Preferably, the vent line 36 is very short and of a substantial diameter such that the solution is circulated over exposed services of the drain check valve 38 and a vent check valve 52. A heating coil 54 adjusts the temperature of the solution. Recirculation continues until the item, the interior of the container, and all exposed surfaces of the tubing system and valves are sterilized.

As the sterilant solution is drained through drain valve 56, sterile air is drawn into the system through an air sterilizing means—preferably a filter that removes any particles the size of a bacteria or larger. The fill valve 14 is opened and the drain valve 56 is closed such that the sterile filter 16 provides a source of sterile rinse. Note that the sterile rinse passes only along sterilized surfaces to assure sterility. The pump 50 circulates the sterile rinse throughout the system. Sterile rinse is drained by opening drain valve 56 again. By closing a valve 60, the pump 50 functions to pump liquid from the system out the drain 40. Additional drain lines (not shown) and aspirators or pumps (not shown) may be provided for removing liquid from all regions of the system.

Figure 3:
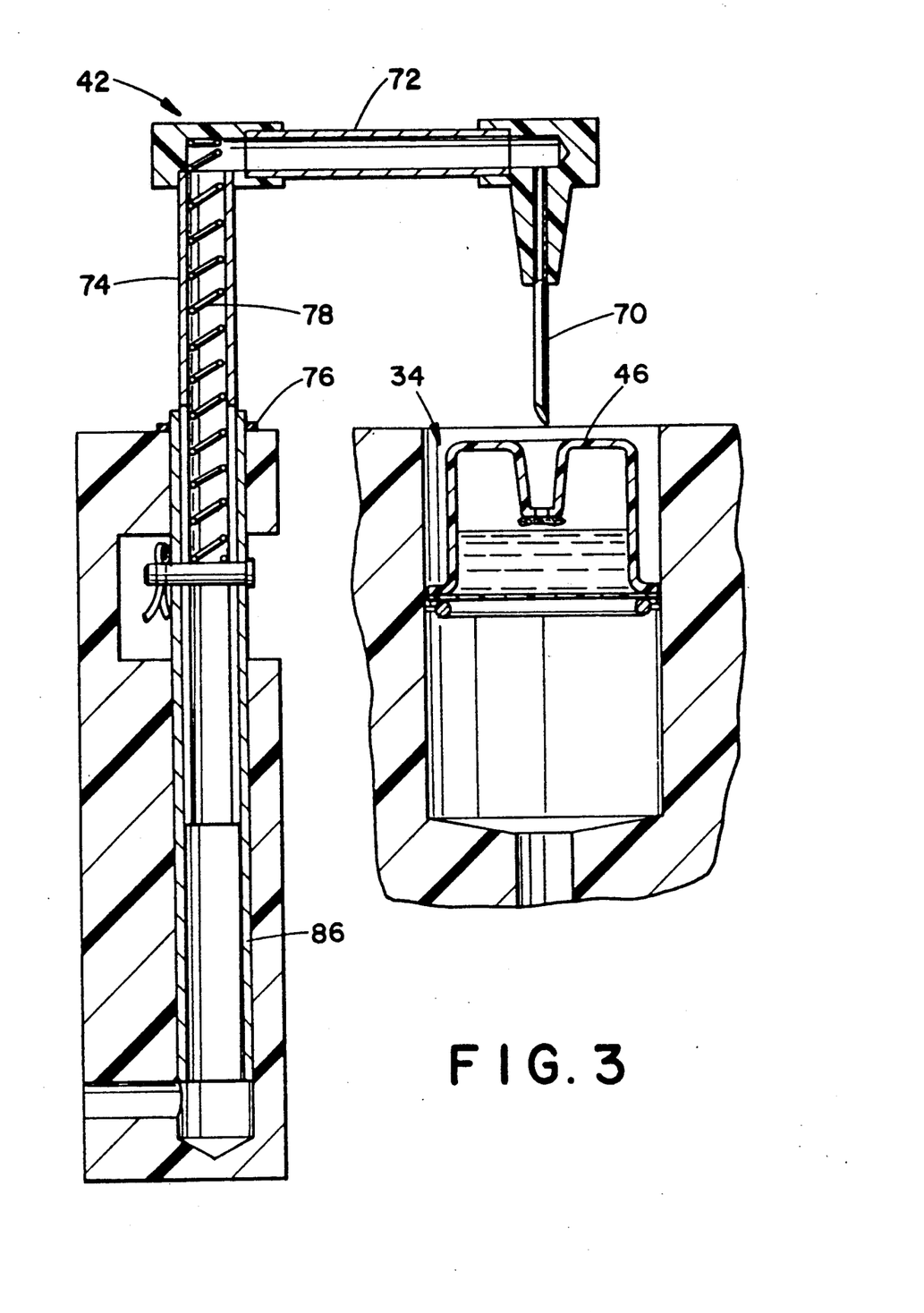
FIG. 3 is a detailed cross sectional view of the aspirator sterilant withdrawal assembly of FIG. 1.

With particular reference to FIG. 3, the sterilant aspirator system 42 includes a hollow, tubular needle or tube 70 which is inserted into the ampule to withdraw the sterilant. The needle 70 is connected with arm 72 which selectively swings the needle into and out of alignment with the ampule 46. A vertical tubular portion 74 is telescopically received in a stationary tubular portion 86. A coil spring 78 biases the arm tubular portion upward, hence, the needle 70 out of contact with the ampule. When the arm is locked into proper alignment with the ampule, closing the lid 24 biases the arm downward against the coil spring 78 forcing the needle 70 into the ampule. Water pumped through the aspirator 44 aspirates the sterilant from the ampule into the fluid flow. Preferably, the aspiration rate is selected such that the sterilant is aspirated gradually over the time required to circulate the water around the system one time.

Figure 4A:
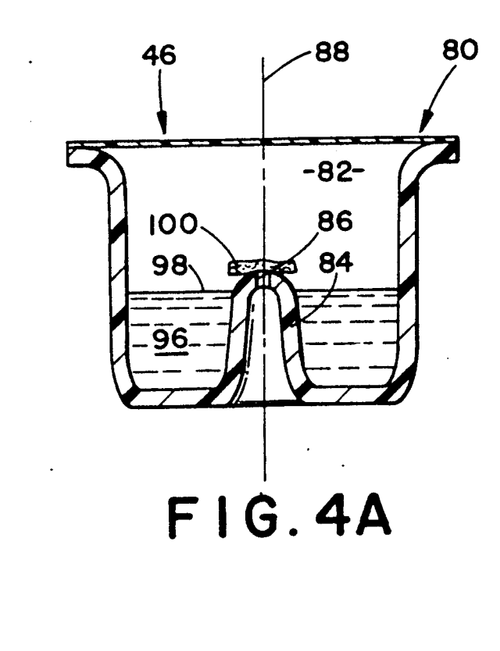
FIG. 4A, 4B, and 4C are detailed cross sectional views of the ampule of FIG. 3 in a range of orientations.
Figure 4B:
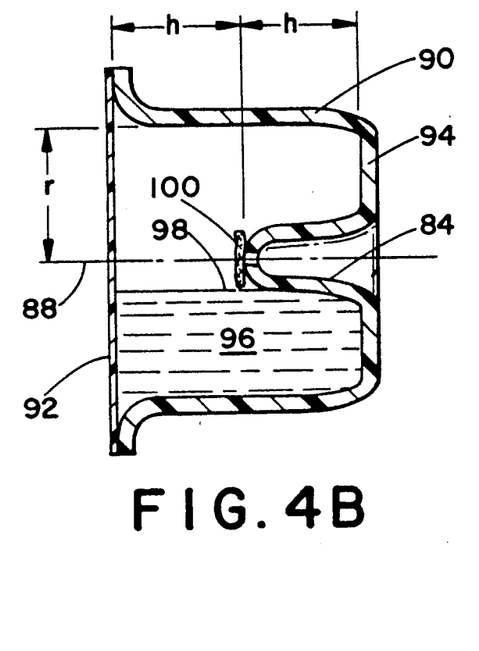
Figure 4C:
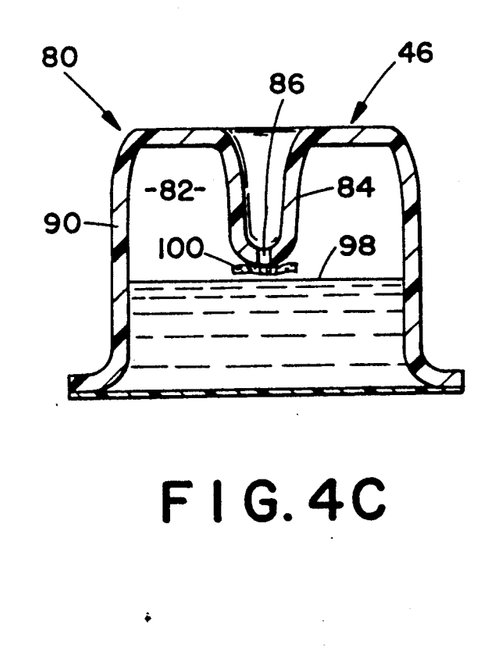

With reference to FIGS. 4A, 4B, and 4C, the sterilant ampule 46 has an exterior wall 80 which defines an interior volume 82 therein. A linear vent passage 84 integral with the exterior wall defines a passage extending linearly from the exterior to a vent aperture 86. In the preferred embodiment, the vent passage extends linearly along a first axis 88 to act as a guide for the needle 70. In this manner, the needle 70 passes through the vent aperture 86 into the interior volume.

In the illustrated embodiment, the exterior wall includes a circularly cylindrical peripheral wall 90 a minimum radius r from the first axis. End walls 92 and 94 extend generally transverse to the axis 88 and are integrally sealed to the peripheral wall. The vent aperture 86 is centrally disposed in the volume. More specifically, the vent aperture 86 is disposed a minimum radial distance r from the peripheral wall and generally a height h from each end wall. The ampule is charged less than half full with a fluid sterilant 96 such that its upper surface 98 is disposed below the vent aperture 86. More specifically, the interior volume 82 is configured relative to the volume of the sterilant such that the sterilant depth is always less than h and r regardless of the orientation of the ampule. In this manner, the liquid does not leak from the vent aperture 86 regardless of the orientation of the ampule 46.

To protect against leakage due to splashing, a porous membrane 100 is disposed across the vent aperture 86. The membrane is a fine woven material which has a median pore size sufficiently small compared to the drop size and wetting ability or surface tension of the liquid sterilant on the fiber material that the sterilant is effectively blocked from passing therethrough. Similarly, water is prevented from flowing freely into the ampule. When the needle 70 passes the vent aperture 86, its cambered end distorts the woven porous material moving the fibers out of its way. The natural resiliency of the fibers tends to return them to their original position when the needle is withdrawn. Any sterilant residue is held in the ampule by the position of the vent aperture 86 and the membrane 100. In this manner, after the sterilization cycle is complete, the operator is protected from contacting the full strength sterilant concentrate directly. Analogously, no dilution of the sterilant concentrate occurs if a sterilizing cycle is aborted before aspiration starts.

With reference again to FIG. 1 and particular reference to FIGS. 5A–D, in operation, the ampule 46 is disposed in the bottom of a see-through larger container 110. The container 110 has a peel-off top 112 which provides access to its contents. The container is shaped such that the ampule 46 fits snugly in the bottom and other powdered reagents 114 are disposed on top.

Figures 5A, 5B:
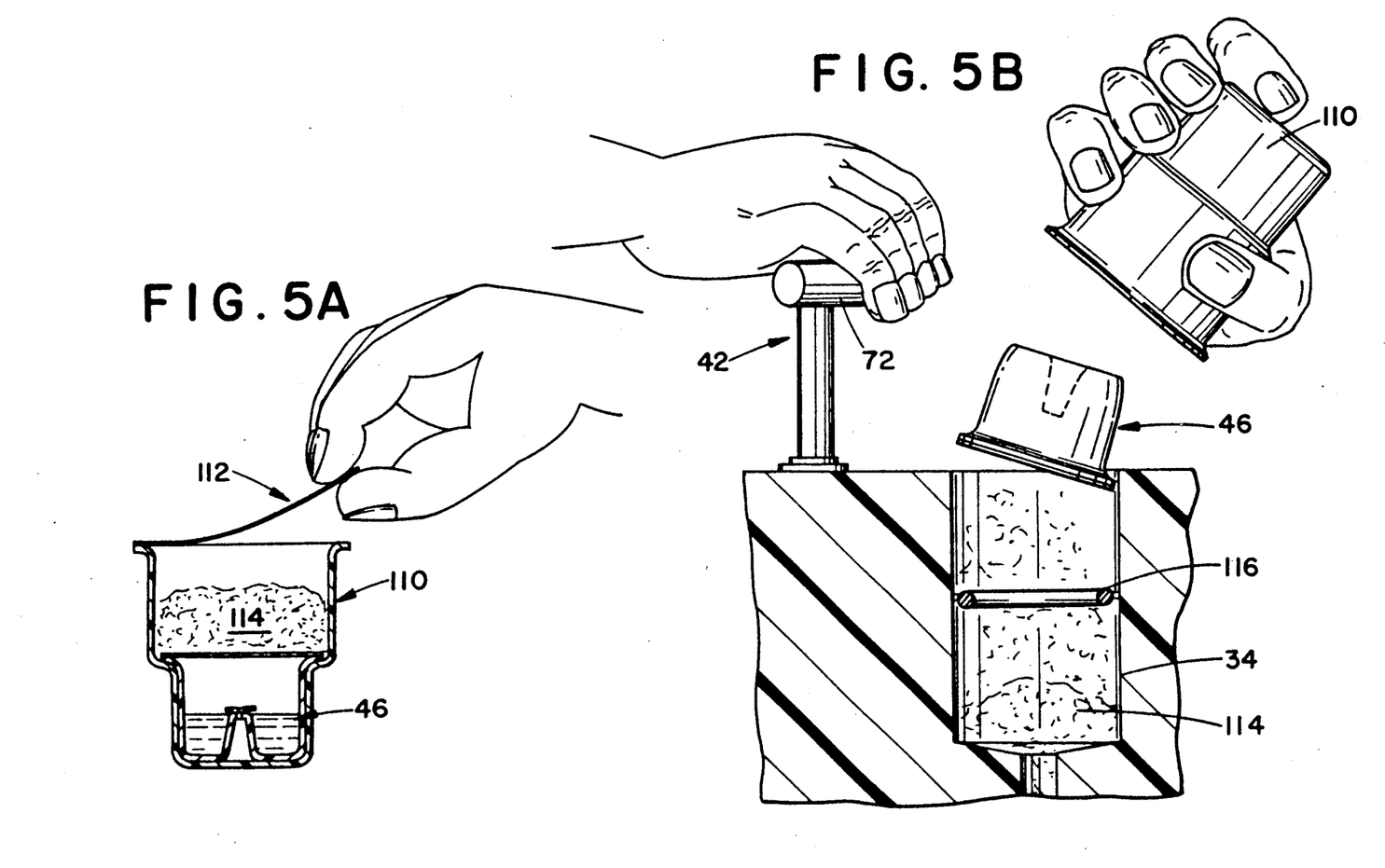
FIGS. 5A, 5B, 5C, and 5D illustrate a preferred method of loading sterilant and powered reagents into the sterilizing apparatus.

In FIG. 5B, the sterilizer arm 72 is swung out of the way and the powdery agents are poured into the well 34. The ampule 46 is supported by rods or other ampule supporting means 116 in a preselected position in the well. In the illustrated embodiment, the ampule is symmetric, thus assuring a central position of the vent aperture 86. Alternately, the support means 126 may include a key or key means which interacts with a selected portion of the ampule to assure proper alignment and positioning.

Figure 5C:
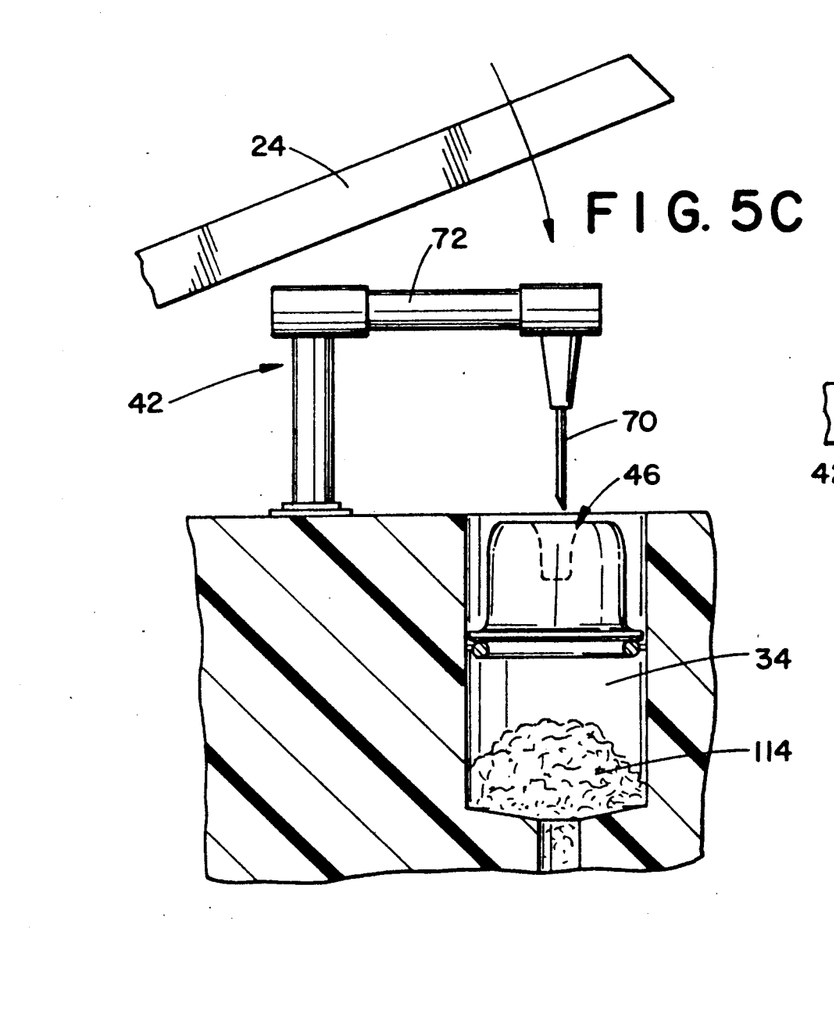
Figure 5D:
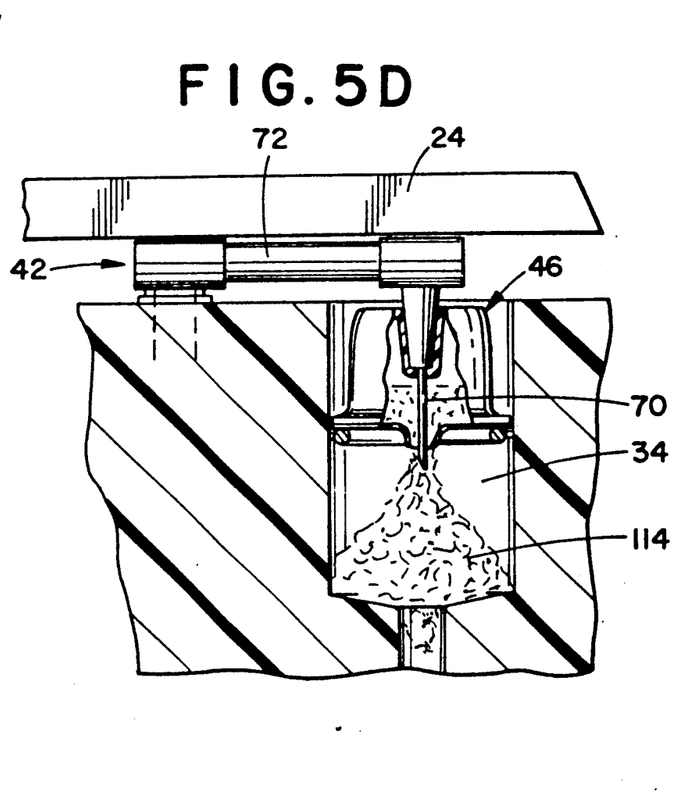

In FIG. 5C, the aspirator arm 72 is swung and locked until the needle 70 is directly over the vent aperture 86. Because the ampule is accurately positioned in the well, the aspirator arm is adjusted to lock itself in the aligned position without hand aligning by the operator. When the lid 24 is closed as in FIG. 5D, the lid cams the aspirator arm against the coil spring 78 moving the tip of the needle 70 through the vent aperture into the proper position within the ampule. Optionally, the ampule may have a small well directly in line with the vent to accommodate the tip of the aspirator needle and assure more complete emptying of the ampule.

In the preferred embodiment, the powdered materials include buffers, detergents, and anti-corrosive agents. The anti-corrosive agents are selected in accordance with the selected sterilant and the nature of the materials in the sterilized items, such as brass fittings, that might be subject to corrosion. Further to the preferred embodiment, the sterilant is peracetic acid. Peracetic acid tends to liberate small quantities of oxygen during transportation and storage. Accordingly, the vent 86 insures that the pressure within the ampule does not become so great that it ruptures. High pressure could also cause spraying of the sterilant upon entry by the needle 70. Once the peracetic acid is diluted and mixed with the buffers, detergents, and corrosion inhibitors, its efficacy as a sterilant is lost after a relatively short duration. The loss of efficacy is much slower than a normal sterilizing cycle, but too short for an ampule containing all the ingredients to have a satisfactory shelf life.

Figure 6:
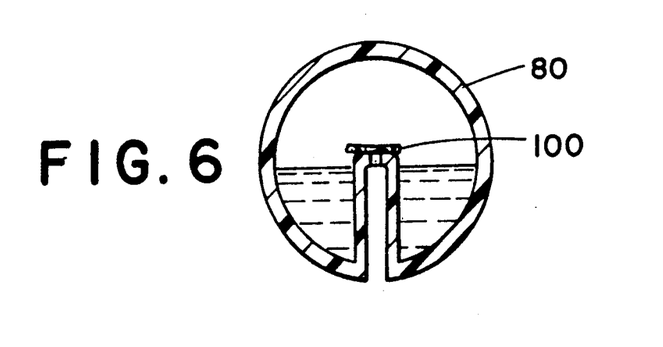
FIG. 6 illustrates an alternate embodiment of a sterilant ampule in accordance with the present invention.
Figure 7:
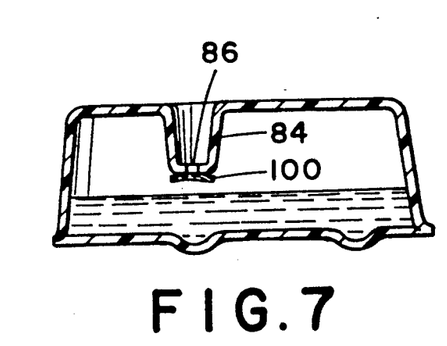
FIG. 7 is another alternate embodiment of the sterilant ampule.
Figure 8:
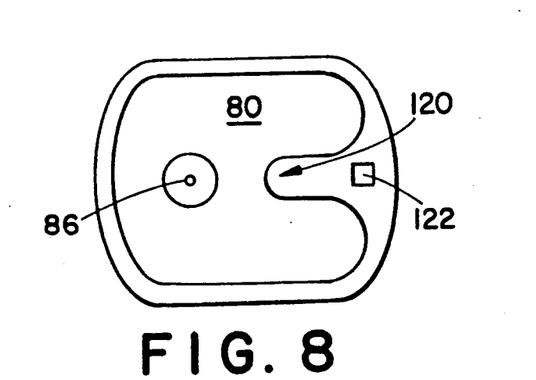
FIG. 8 is a top view of yet another alternate embodiment of the sterilant ampule; and, FIG. 9 illustrates an alternate reagent discharging apparatus.

With reference to FIGS. 6, 7, and 8, the ampule may take various shapes. For example, as shown in FIG. 6, the exterior wall 80 may be spherical. The vent aperture is still disposed in the center of the sphere and the fill level is such that the depth of the sterilant is smaller than the radius of the spherical interior volume. Alternately, as illustrated in FIG. 7, the vent aperture may be disposed eccentrically. However, the vent aperture is still disposed sufficiently close to the center of the interior volume that for the volume of sterilant provided, the upper surface of the sterilant always remains below the vent aperture. As yet another alternative, as shown in FIG. 8, the ampule may have a groove or key way 120 in the exterior wall or a groove or aperture 122 in an exterior flange to assure that the ampule is disposed in a preselected alignment. By selecting a sufficiently fanciful or arbitrary exterior shape or key pattern, protection can be had against inserting generally round ampules from other equipment which might contain substances other than sterilants.

Figure 9:
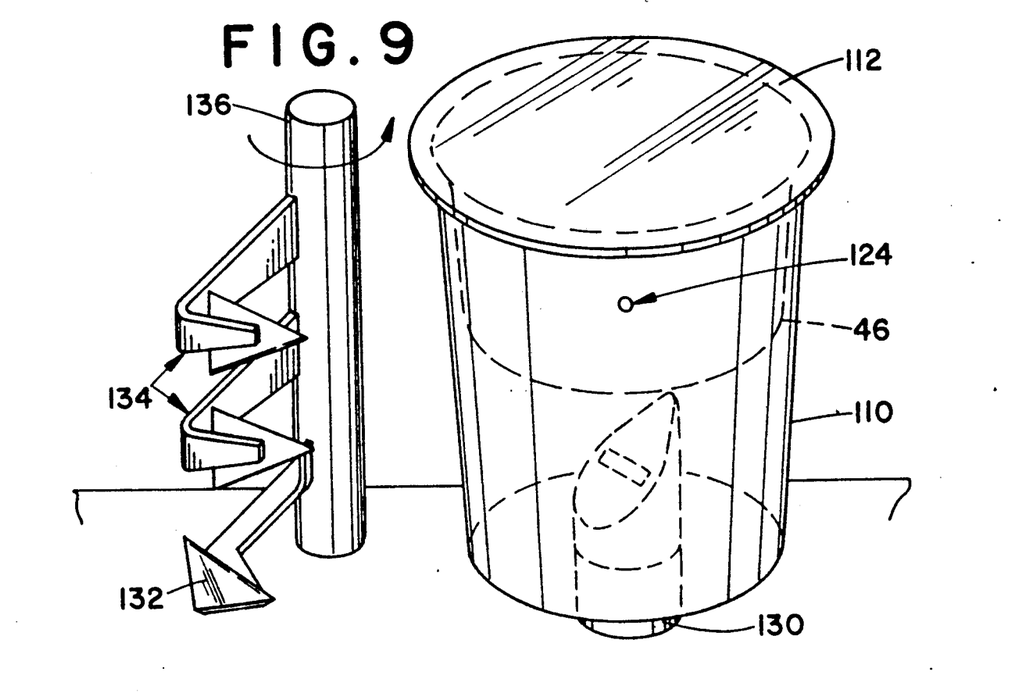

With reference to FIG. 9, the sterilant, buffer, detergent, anti-corrosives, and other reagents may be retrieved from a two compartment container in other ways. For example, the liquid containing ampule 46 may be mounted in the upper portion of a clear plastic cup 110 with the powdered components or reagents 114 in the lower portion. The powdered components are selected to include a material which changes color upon exposure to the liquid components. In this manner, a visual check is provided that the liquid components have not leaked into the powdered components. A vent 124 in the outer cup provides communication between the ampule and the atmosphere. Rather than siphoning out the liquid sterilant, a first puncturing ram 130 can extend into the lower part of the cup to introduce water or other dilutant into the cup and dissolve the powdered reagents. Additional water flow into the cup may be had when a first cutter 132 cuts the cup allowing water pumped into the well to circulate through the powder region of the cup. Movement of additional cutters 134 pierce both the cup and the sterilant ampule. In this manner, the powdered ingredients can be dissolved and mixed with recirculating water or other dilutant before the sterilant is released. In the illustrated embodiment, cutters 132 and 134 are mounted on a common shaft 136 which is incrementally rotated to cause staged cutting of the cup and the ampule.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A liquid mixing system comprising:
   an ampule having a vent passage that defines a vent aperture adjacent one end and an exterior wall that surrounds the vent aperture to define an interior volume such that the vent aperture is located in a generally central region of the defined volume;
   a dilutant source for providing a flow of a dilutant liquid;
   a liquid reagent partially filling the ampule interior region, an upper surface of the liquid reagent being disposed out of contact with the vent aperture such that the liquid reagent does not drain by gravity from the ampule through the vent aperture; and, a liquid reagent discharging means for discharging the liquid reagent from the ampule interior volume into the dilutant flow.

2. The system as set forth in claim 1 wherein the ampule further includes a gas passing, fluid blocking membrane, mounted across the vent aperture such that gas is vented from the ampule interior volume while the liquid reagent is retained.

3. The system as set forth in claim 1 wherein the vent passage is disposed linearly along a first axis.

4. A liquid mixing system comprising:
an ampule having:
a vent passage extending along a first axis, the vent passage extending between a vent aperture adjacent a first end and an exterior wall adjacent a second end,
a liquid agent contained in the ampule exterior wall, the ampule exterior wall
including a peripheral wall disposed at least a minimum radius r from the first axis and a pair of end walls disposed generally transverse to the first axis and sealed peripherally to the peripheral wall, the end walls each being separated from the vent aperture along the first axis by a distance h, the liquid reagent having a depth of less than h when the first axis is disposed vertically and less than r when the first axis is disposed horizontally, whereby the surface of the liquid reagent is maintained below the vent aperture in either orientation to permit venting of gases without discharging the liquid reagent;
a dilutant source providing a flow of a dilutant liquid; and,
a liquid reagent discharging means for discharging the liquid reagent from the ampule interior volume into the flow of dilutant liquid.

5. The system as set forth in claim 4 wherein the discharging means includes:
a tubular member which is mounted for reciprocating movement along the first axis, the tubular member being movable between a first position in which a free end is displaced from the ampule and a second position in which the free end has passed through the vent aperture and is disposed within the liquid reagent; and,
a means for moving the liquid reagent through the tubular member and into the flow of dilutant liquid.

6. The system as set forth in claim 5 wherein the liquid reagent moving means includes an aspirator such that the flow of dilutant liquid aspirates the liquid sterilant thereinto.

7. The system as set forth in claim 4 further including a reservoir holding a second reagent, the reagent discharging means being operatively connected with the reservoir for selectively intermixing the second reagent with the flow of dilutant liquid.

8. The system as set forth in claim 7 wherein the second reagent is a dissolvable powder and wherein the discharging means causes at least a portion of the flow of dilutant liquid to flow through the reservoir dissolving the second reagent.

9. A liquid mixing system comprising:
an ampule having a vent passage that defines a vent aperture adjacent one end and an exterior wall that surrounds the vent aperture to define an interior volume such that the vent aperture is located in a generally central region of the defined volume;
a dilutant source for providing a flow of a dilutant liquid;
a sterilant liquid partially filling the ampule interior region, an upper surface of the liquid sterilant being disposed below the vent aperture;
a reservoir holding at least one of a buffer, detergent, and anti-corrosive;
a discharging means operatively connected with the reservoir for discharging the liquid sterilant from the ampule interior volume into the dilutant flow; and,
a container for receiving an item to be sterilized disposed in fluid communication with the dilutant flow downstream from the discharging means such that a sterilant composition is caused to fill the container and sterilize the received item.

10. The apparatus as set forth in claim 9 further including:
a source of sterile rinse fluid;
a tubing array for connecting the source of sterile rinse fluid with the container; and,
a recirculating means for recirculating the dilutant and sterilant through the tubing array such that sterile rinse fluid from the sterilant rinse source flows into the chamber through the tubing array which has been sterilized.

11. An ampule comprising:
a vent passage defining a vent aperture at a first end thereof;
an exterior wall encompassing the vent aperture in three dimensions and defining an interior volume within the exterior wall, the exterior wall defining an aperture that is surrounded by a second end of the vent passage, the vent passage being sealed to the exterior wall such that the interior volume is vented through the vent passage to an exterior of the exterior wall, the exterior wall and the vent aperture being positioned relative to each other such that the vent aperture is disposed centrally in three dimensions in the interior volume such that when a fluid partially fills the volume, its upper surface remains out of contact with the vent aperture and the fluid does not drain by gravity through the vent passage in any orientation of the ampule.

12. An ampule comprising:
an exterior wall surrounding and enclosing an interior volume, the interior volume having a geometric center that is generally equidistant from opposite points of the exterior wall;
a vent passage connected with the exterior wall adjacent a first end and extending into the interior volume, the vent passage defining an open vent aperture adjacent the geometric center and defining a vent passage between the vent aperture to an exterior of the exterior wall;
a liquid reagent partially filling the interior volume such that an upper surface of the liquid regent remains out of contact with the vent aperture regardless of an orientation of the ampule, whereby gases are freely vented from the interior volume to the exterior of the exterior wall while the liquid reagent is retained within the exterior volume.

13. The ampule as set forth in claim 12 further including a porous woven material spanning the vent aperture.

14. An ampule comprising:

a vent tube which acts as a guide for a hollow tube passing therealong defines a vent aperture at a first end thereof;

an exterior wall connected with a second end of the vent tube and surrounding the vent tube and the vent aperture and defining an interior volume;

a liquid partially filling the interior volume such that a surface of the liquid is out of contact with the vent aperture and the liquid does not drain by gravity through the vent tube in any orientation of the exterior wall.

15. The ampule as set forth in claim 14 wherein the ampule is partially filled with peracetic acid and wherein the ampule is disposed in a second container having a second vent aperture therein, the second container further including a powdered reagent including at least one member of the group consisting of a buffer, a detergent, and an anti-corrosive agent.

* * * * *